United States Patent
Alt et al.

[11] Patent Number: 5,876,408
[45] Date of Patent: Mar. 2, 1999

[54] METHOD FOR ENHANCING IMPLANTATION OF THIN LEADS

[75] Inventors: Eckhard Alt, Ottobrunn, Germany; Lawrence J. Stotts, Lake Jackson, Tex.

[73] Assignee: Sulzer Intermedics, Inc., Angleton, Tex.

[21] Appl. No.: 874,037

[22] Filed: Jun. 12, 1997

[51] Int. Cl.⁶ .................................................. A61B 17/22
[52] U.S. Cl. ............................................................ 606/129
[58] Field of Search .................................. 606/129, 108, 606/172, 130

[56] References Cited

U.S. PATENT DOCUMENTS

| | | | |
|---|---|---|---|
| 4,633,880 | 1/1987 | Osypka et al. | 606/129 |
| 4,791,939 | 12/1988 | Maillard | 606/129 |
| 4,832,048 | 5/1989 | Cohen | 606/129 |

*Primary Examiner*—Michael Buiz
*Assistant Examiner*—Kevin Truong
*Attorney, Agent, or Firm*—Blank Rome Comisky & McCauley LLP

[57] ABSTRACT

A method of implanting small diameter conductive leads for an artificial cardiac pacemaker or other body-implantable medical device includes inserting the lead to be implanted into a predetermined path within the patient's body with the assistance of a stylet for guiding the lead along the path. At least a portion of the stylet which is to traverse the path has an enhanced radiopaque characteristic attributable to the application or addition to the material of which the stylet is composed, of a substance having such radiopaque characteristic. When viewed under fluoroscopy external to the patient's body as the lead is maneuvered along the path, although the thin lead itself may be difficult to see, the stylet is readily discernible by virtue of its enhanced radiopacity, thereby enabling the physician to position the lead at a desired location within the patient's body. For various reasons, the thin lead itself may not be amenable to similar enhancement, which makes the stylet a suitable solution. A portion of the distal end of the stylet, such as its distal tip or a plurality of spaced apart points along its distal end, is provided with the enhanced radiopacity, as by application or addition of gold to the stylet material.

10 Claims, 1 Drawing Sheet

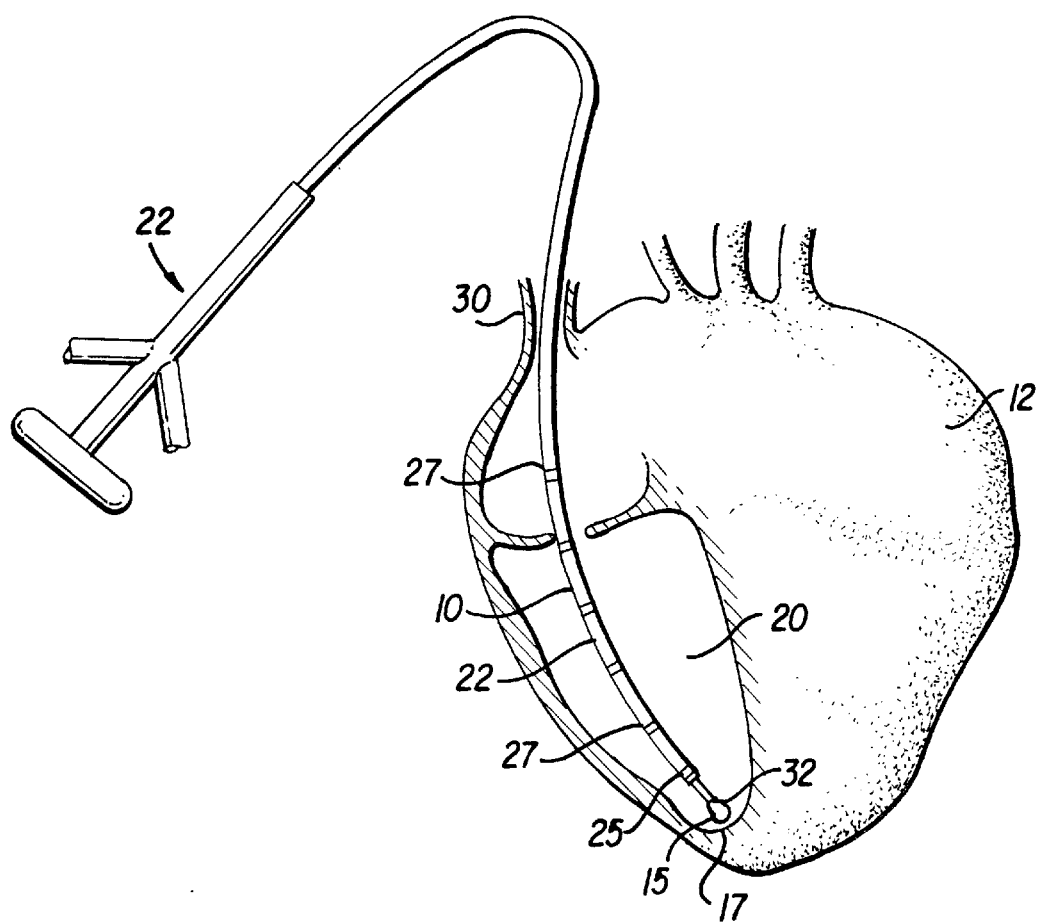

METHOD FOR ENHANCING IMPLANTATION OF THIN LEADS

BACKGROUND OF THE INVENTION

The present invention relates generally to improvements in implantation of electrically conductive leads in the human body, and more particularly for enhancing the capability to implant leads of extremely small diameter into precise locations within the patient's cardiovascular system or other positions within the body.

As the technology of implantable medical devices has progressed, advances in the technology of electrical leads associated with such devices have produced improvements in lead functionality and maneuverability, and reduction in lead failure rates. The advances in lead technology include a considerable reduction in lead diameter achieved by means of multi-filar wound coils, redundancy, and bipolar leads in which the individual leads are run, not coaxially, but as separate parallel Teflon-insulated wires in a space-wound manner. These leads are referred to as Thin-Line™ leads by the manufacturer, Intermedics, Inc. of Angleton, Tex. ("Thin-Line" is a trademark of Intermedics, Inc. for its small diameter leads).

A principal advantage of such thin leads and the composite configurations in which they are run is that the lead—single or composite—can be introduced into and advanced through blood vessels of much smaller lumen diameter than was admissible by leads of the prior art. For example, a Thin-Line bipolar lead may be provided with a size 6 to 7 French body, which can be accommodated by a 2.0 to 2.3 millimeter (mm) lumen, compared to a typical prior art bipolar lead for similar use which has a size 10 to 12 French body that requires a vein of 3.0 to 3.5 mm lumen diameter. Patients' vein sizes differ, and, for various reasons, not all patients are able to accommodate the 10 or 12 French lead sizes that heretofore had to be used in certain blood vessels of the body. As expected, the smaller diameter lead is more likely to be successfully accepted and advanced through the smaller natural venous access following a venous cutdown. Further, in procedures such as puncture and subclavian stick, the size of the puncture aperture and number of potential complications attributable to it are a function of the diameter of the lead to be introduced. A 2.0 mm puncture wound in a subclavian vein, for example, is likely to create considerably fewer problems than a 3.0 mm puncture.

Although improvements abound in procedural aspects and risk reductions from the use of these smaller diameter leads, as the French size of such a lead is decreased, the lead becomes considerably less visible under X-ray fluoroscopy during surgical and medical implant procedures. Consequently, it is more difficult for the physician to maneuver a thin lead associated with a cardiac pacemaker device, for example, into a desired position in a heart chamber, such as at the apex of the right ventricle.

It is a principal aim of the present invention to provide improvements in techniques by which the capability to use such small diameter leads in situations requiring extremely precise placements may be considerable enhanced.

SUMMARY OF THE INVENTION

One solution for enhancing the capability to implant leads of very small French size would be to increase the visibility of the lead body under X-ray fluoroscopy by applying to its surface or portions of its surface a substance that is more radio-opaque, i.e., has greater radiopacity (radiopaque), than that of the materials commonly used in the electrically conductive wires for the leads themselves, such as stainless steel or the medical grade alloys such as NP35. For example, gold has a radiopacity level about five times greater than that of an equally-sized elongate body of stainless steel.

By coating at least a part of the lead body with gold or other material of higher radiopacity, then, the lead would be much more visible to the surgeon during the implant procedure. But although it is quite biologically compatible with the blood and tissue of the body, gold is expensive, so that the cost of leads treated with that element would be subject to large increases in price to the medical community and, ultimately, to the patient. In an era in which considerable effort is being made to intelligently reduce the cost of medical devices and procedures, this would be counterproductive.

Another objective of the invention is to enhance the capability to accurately implant leads of extremely small French sizes without thereby significantly increasing the cost of the lead.

On the other hand, severe adverse chemical reactions and interactions have been found to occur with various other potential radiopaque coatings and typical lead insulation materials such as silicone, polyurethane, or Teflon. It has been found, for example, that serious undesirable interaction takes place between silver and polyurethane, which results in cracking and fractures in the lead insulation that causes electrical short circuiting ("shorting") and other failures of the leads.

It is another aim of the invention, then, to enhance the techniques for implantation of small-sized leads without adverse effect on the reliability or integrity of the lead itself.

According to the invention, the above and other aims and objectives are achieved by enhancing the visibility of the stylet that is generally used implant the lead. A stylet is typically introduced into the venous system while the lead is being inserted and maneuvered into place, and the stylet is then removed. The stylet is a reusable adjunct, and, to that end, is sterilized between procedures. It is also generally composed of materials which would not suffer adverse reaction from use of radiopaque coatings, or indeed, it could be composed of one or materials which themselves are sufficiently radiopaque to serve the ends of the present invention. Although the stylet is typically of larger size diameter than the leads with which it is to be used, it, too, can be of such small French size as to be barely visible under fluoroscopy, so that the visibility enhancement provided by the invention is of substantial significance in improving lead implantation.

BRIEF DESCRIPTION OF THE DRAWING

The above and still further aims, objectives, features, aspects, and attendant advantages of the invention will become apparent from a consideration of the following detailed description of a presently contemplated best mode of practicing the invention, with reference to a presently preferred embodiment and method thereof, especially when taken in conjunction with the accompanying drawing in which the sole FIGURE is a partial view, in perspective, of a stylet and illustrating its use in implanting a lead in the cardiovascular system.

DETAILED DESCRIPTION OF THE PREFERRED EMBODIMENT AND METHOD

In the sole FIGURE, a pacemaker lead 10 is being introduced into the patient's heart 12 so that a distal electrode 15 of the lead will be positioned at the apex 17 of the right ventricle 20. In this implantation procedure, it is customary practice to use a stylet 22 to aid the implanting physician in precisely advancing and positioning the lead 10, and in placing the electrode 15 at its desired location. Where an electrode is used for both stimulation and sensing electrical activity of a chamber of the heart, for example, pacing pulses are delivered from the implanted pacemaker (not shown) through the pacemaker lead 10 and to the distal electrode 15.

For the electrode to stimulate ("capture") excitable tissue in the chamber, it must be positioned in suitable proximity to the tissue so as to transfer electrical energy from the incoming pulses to the tissue with sufficient efficiency to avoid substantial loss of energy in the transfer, and thereby, to permit the pulse energy-generating circuitry and components thereof, as well as the batteries, in the pacemaker generator to be of sufficiently small size for practical application as an implantable device. Similar considerations apply to the sensing aspect of the electrode, in which the electrical field developed at the intrinsically- or extrinsically-excited tissue is accurately and efficiently detected to generate a sense signal which is carried by the lead (along a different wire from that used to deliver the pacing pulses) to detection circuitry including a sense amplifier in the pacemaker generator.

Energy efficiency demands proper positioning and placement of the lead and electrode(s) in such a situation. In other applications, it may be considerations of placement of the lead itself such as advancement along a particular desired path, or the placement of other associated elements such as an anchoring balloon in a certain application, that dictate a desired location. These, of course, are merely examples, and not intended to be limiting in any way.

According to the invention, stylet 22 is, at least in part—such as at its tip 25 and at intervals 27 which may or may not be uniformly spaced—coated or filled with or composed of material(s) adapted to increase its radiopacity. The extent of this enhanced radiopacity should be sufficient to render the entire stylet or the regions of it readily visible to the implanting physician, despite the fact that the lead (catheter, or the like) which the stylet is being used to introduce and advance is not readily visible under fluoroscopy. For example, a standard stainless steel stylet composed of 316 stainless or other biocompatible alloy, has a diameter in a range of between about 0.012 and about 0.016 inch, most commonly 0.014 inch. In any event, the typical stylet is not greatly visible under fluoroscopy, nor is the lead.

The visibility of the stylet is increased by this coating, filling, attaching to, or introducing into (during manufacture of) the stylet a substance or material such as gold, cobalt, platinum, algilloy, barium, and steel alloys or other element (s) which have high radiopacity (including alloys and mixtures). For example, the added substance should preferably increase the radiopacity of the stylet by about a factor of five, or even more. In those circumstances, the visibility of the stylet under fluoroscopy would similarly be increased or enhanced by a factor of about five, relative to the same stylet composed of a material of the lesser radiopacity, such as stainless steel.

Since gold is not irritating to tissue, and is virtually non-allergenic, gold can be a good choice for a radiopaque material for enhancing the radiopacity of a device or material to be implanted, where the patient suffers with severe materials allergies. The superior radiopaque qualities of the noble metal assure that implanted object can be observed by fluoroscopy, without difficulty, during its advancement through the superior vena cava 30 or other vessel lumen to the desired site of deployment. Also, a gold surface possesses substantially non-thrombogenic characteristics, so that it will reduce the likelihood of a closure of the vessel in which it is implanted.

Gold does have disadvantages of reduced mechanical strength and high relative cost compared to non-noble metals. However, by manufacturing the lead or other device with a core or main body substantially entirely composed of material of relatively low cost, such as stainless steel, and of superior mechanical properties compared to noble metals, the strength and cost concerns are eliminated.

In an exemplary preferred embodiment, the stylet includes a hollow tube 28 of, for example, 0.014 inch lumen (i.e., inner) diameter. The lumen of this tube is treated with the more radiopaque substance, such as wolfram, barium, or gold, which might even be in the form of a wire. The entire lumen need not be filled with the radiopaque material, but only a strategically located portion thereof such as the distal end 25. If other portions are also used (as at 27), they may be separated by lengths of biologically compatible, but less expensive segments of material. In the preferred embodiment, the more radiopaque material is confined to the distal end of the device, which reduces manufacturing costs and, therefore, the price of the stylet, particularly where a more expensive radio-dense material such as gold is used. In that case, the gold is preferably limited to the last ten or twenty centimeters (cm) at the distal end of the stylet. This more radiopaque portion of the length allows the implanting physician to clearly visualize from the fluoroscope where the typically 60 cm length of lead for the right ventricular apex placement ends distally.

In an alternative embodiment, the more radiopaque material is hermetically embedded, in the form of particulate matter, into a small ball-type tip, such as 25, of the stylet.

The insertion of the radiopaque-enhancing substance internally of the stylet is preferred over use of a coating, an attachment, or an additive to the material of which the stylet is manufactured. In the case of a coating or an attachment, if the stylet were to undergo substantial bending or other stress, it is possible that tiny fractures might occur in the coating so that particulate matter is released. This is undesirable from a standpoint of pure biological considerations, as well as from the possibility that such particulate matter could interact adversely with the electrical insulation material such as silicone rubber, polyurethane, or Teflon on the lead sought to be introduced and advanced with the stylet to cause a long term lead failure mechanism. Introducing a special radiopaque substance into the composition from which the stylet is formed, as a change to the method of manufacture of the stylet, could affect other parts of the manufacturing process sufficiently to impose various changes in materials treatment, and so forth, so it is a less desirable technique than simply inserting the radiopaque material into the lumen. However, each of these techniques could be alternatively employed, with appropriate safety measures, rather than insertion of the substance into the lumen. In the preferred technique, the radiopaque or radio-dense material is confined internally of the stylet by means of hermetic sealing, which is one type of safety measure that is readily and inexpensively achieved.

Modification of an existing stylet may also be done for the sake of employing the principles of the present invention. A typical retraction stylet has an inner retraction wire that extends through the lumen of the stylet to operate an anchoring mechanism. This type of stylet may be provided with the structural characteristics of the invention by replacing the retraction wire with the more radiopaque material, since the retraction wire is not needed where the stylet is being used to position a lead.

When the pacing lead of the sole FIGURE of drawing herein is to be inserted into the patient's vascular system, and its distal tip advanced into the apex 17 of the right ventricle 20, for example, the stylet is inserted all the way except for the very tip of the lead. For that reason, i.e., because some tiny portion of the distal end of the lead may yet remain difficult to see despite the more radiopaque end of the stylet, it may also be desirable to incorporate a similar radiopaque substance at or adjacent to the very the tip 32 of the distal end of the wire, at or very near the point where it is swaged or crimped to make electrical connection to the electrode. This provides a good radiopaque marker to aid visualization by the fluoroscopic image of the total length of the lead, which includes the radiopaque stylet, plus the radiopaque portion at the tip of the lead. Subsequently, when the stylet is retracted, the physician is still able to observe at least the distal tip of the lead.

From the foregoing, it will be seen that a method has been disclosed for enhancing the capability to implant small diameter conductive leads associated with an artificial cardiac pacemaker or other body-implantable medical device, for the purpose of an implant procedure in which such leads are maneuvered into position in the cardiovascular system of a patient by means of fluoroscopy. The method includes inserting a stylet into the cardiovascular system to assist in maneuvering the lead, the stylet having increased radiopacity by virtue of at least one predetermined portion of its structure having an added substance of greater radiopacity than that of the material of which the stylet is generally composed. Further, the method involves maneuvering the lead with the stylet through a preselected portion of the cardiovascular system under fluoroscopy so that the increased radiopacity of the stylet provides greater visibility of the procedure to achieve the desired positioning of the lead.

In use of the method, the stylet may include a hollow tube, in which the added substance of greater radiopacity is located in at least a portion of a longitudinal passage, and the substance is sealed therein to prevent its escape during use of the stylet, and may, if desired, be hermetically sealed within the hollow tube. The addition of a substance or substances to enhance the radiopaque character of the stylet should avoid producing any substantial adverse effect on the physical handling characteristics of elasticity and flexibility of the stylet if it were used without such added substance(s). The addition is preferably to the distal portion of the stylet only. A suitable substance may be selected from the group consisting of gold, platinum, algilloy, cobalt, barium, and steel alloy, or mixtures thereof. The method may be practiced using a lead which has a distal end of greater radiopacity than that of the remainder of the lead, so that the distal end of the lead is more visible under fluoroscopy than the remainder of the lead.

The method may alternatively be characterized as being for implanting small diameter conductive leads for an artificial cardiac pacemaker or other body-implantable medical device, and as including steps of inserting a lead to be implanted along a predetermined path within the patient's body with the assistance of a device for guiding the lead along the path, at least a portion of the device which is to traverse at least a portion of the path being characterized by an enhanced radiopacity substantially greater than the radiopacity of the lead being implanted, and maneuvering the lead along the path while viewing external to the patient's body the location of at least the portion of the device by virtue of its enhanced radiopacity, to position the lead at a desired location within the patient's body. Typically, the device is a stylet, and the path includes a natural lumen in the patient's body.

A method for enhancing the visibility of the stylet for use in implanting in a patient's vascular system a lead having little or no visibility under fluoroscopy, includes incorporating a substance of substantially greater radiopacity than that of the stylet alone with the material of which the stylet is composed, and maintaining the substance in place on the stylet to inhibit escape therefrom. In this method, the stylet is a hollow tube, the incorporated substance of greater radiopacity is inserted into at least a portion of an axial passage of the hollow tube, and the substance is hermetically sealed therein to inhibit its escape thereof during use of the stylet.

A device to assist implanting small diameter conductive leads for an artificial cardiac pacemaker or other body-implantable medical device in a patient's body includes an elongate body having a proximal end which is to be remain outside the patient's body when the device is in use, and having a distal end which is adapted to retain the lead for guidance during implantation thereof along a predetermined path within the patient's body. A portion of the distal end of the body of the device, such as the distal tip thereof or a plurality of spaced apart points along the distal end of the device, is of substantially greater radiopacity than the radiopacity of at least a substantial majority of the structure of the lead to be implanted, to enable viewing from a vantage point external to the patient's body the location of at least the portion of the device by virtue of the greater radiopacity thereof, and thereby to enhance positioning of a remote point on the lead at a desired location within the patient's body.

A portion of the proximal end of the body of the device includes means for controlling the guiding of the lead during implantation thereof along the predetermined path.

Although a presently preferred embodiment and method of the invention has been disclosed herein, it will be apparent to those skilled in the art that variations and modifications of the described embodiment and method may be made without departing from the spirit and scope of the invention. Accordingly, it is intended that the invention shall be limited only by the appended claims and the rules and principles of applicable law.

What is claimed is:

1. A stylet to assist implanting a small diameter conductive lead for an artificial cardiac pacemaker or other body-implantable medical device in a patient's body, the stylet comprising:

an elongate body having a proximal end which is adapted to be positioned outside the patient's body when the stylet is in use, and having a distal end which is adapted to detachably retain the lead for guidance during implantation thereof along a predetermined path within the patient's body and to be selectively detached from the lead upon positioning of a predetermined remote point on the lead at a desired location within the patient's body to permit retraction of the stylet from the body while leaving the lead implanted therein, a portion of the distal end of the body of said stylet being of substantially greater radiopacity than the radiopacity of at least a substantial majority of the lead to be implanted, to enable viewing from a vantage point external to the patient's body the location of at least said portion of the stylet under fluoroscopy by virtue of the greater radiopacity thereof, and thereby to enhance the capability for said positioning of the predetermined remote point on the lead at said desired location within the patient's body despite the relatively lower radiopacity and consequent reduced visibility of the lead itself under fluoroscopy, and a portion of said proximal end of the body of the stylet including means for controlling the guiding of the lead during implantation thereof along said predetermined path within the patient's body.

2. The stylet of claim 1, wherein said portion of the distal end of said elongate body is the distal tip of the stylet.

3. The stylet of claim 1, wherein said portion of the distal end of said elongate body is a plurality of spaced apart points along the distal end of the stylet.

4. The stylet of claim 1, wherein said portion of the distal end of said elongate body of substantially greater radiopacity comprises a portion incorporating a material of substantially greater radiopacity than any other portion of said elongate body.

5. The stylet of claim 1, wherein said portion of the distal end of the elongate body comprises a hollow tube, and a substance of said greater radiopacity applied along a surface of at least part of a longitudinal passage of the hollow tube, said substance being sealed along said surface to prevent its escape during use of the stylet.

6. The stylet of claim 5, wherein said substance is hermetically sealed within the surface of said longitudinal passage of the hollow tube.

7. A reusable stylet for implanting in a patient's body an electrical lead to be used with an artificial cardiac pacemaker or other body-implantable medical device, wherein the lead is of a thinness and radiopacity which render it of low visibility under fluoroscopy, said stylet comprising:

an elongate body having a proximal end adapted to be located outside the patient's body and including a control means adapted, when operated, to enable the lead to be temporarily secured to the elongate body for guidance and manipulation thereby when the stylet is in use, said elongate body having a distal end including retention means adapted to detachably retain the lead for guidance and manipulation during operation of said control means to enable advancement of the lead along a predetermined path within the patient's body during implantation thereof, said distal end of the elongate body including at least one portion thereof composed of a material which is sufficiently radiopaque to be highly visible under fluoroscopy, whereby to enable viewing a lead when secured to said elongate body on fluoroscope by reference to said radiopaque portion of the distal end of the elongate body for positioning a distal point on the lead at a preselected implanted location within the patient's body to remain thereat when said control means is selectively operated to detach the lead from said elongate body in preparation for retraction of the stylet.

8. The reusable stylet of claim 7, wherein said radiopaque portion of the distal end of the elongate body is located at the distal tip of the elongate body.

9. The reusable stylet of claim 7, wherein said radiopaque portion of the distal end of the elongate body includes a plurality of spaced apart regions of said radiopaque material along said distal end.

10. The reusable stylet of claim 7, wherein said distal end of the elongate body comprises a hollow tube portion, and said radiopaque material is sealed along an inner surface of said hollow tube portion to prevent escape thereof during use of the stylet.

* * * * *